United States Patent [19]

Ort et al.

[11] Patent Number: 5,106,980
[45] Date of Patent: Apr. 21, 1992

[54] PREPARATION OF QUINOPHTHALONES

[75] Inventors: Burkhard Ort, Wachenheim; Guido Kuth, Ludwigshafen, both of Fed. Rep. of Germany

[73] Assignee: BASF Aktiengesellschaft, Ludwigshafen, Fed. Rep. of Germany

[21] Appl. No.: 722,171

[22] Filed: Jun. 27, 1991

[30] Foreign Application Priority Data

Jun. 27, 1990 [DE] Fed. Rep. of Germany ....... 4020423

[51] Int. Cl.$^5$ .......................................... C07D 403/02
[52] U.S. Cl. .................................. 546/167; 548/473; 546/173
[58] Field of Search ........................................ 546/167

[56] References Cited

U.S. PATENT DOCUMENTS 3,662,583  11/1971  Dehnert ........................ 260/287 R

FOREIGN PATENT DOCUMENTS 1770960  1/1972  Fed. Rep. of Germany .
2230601  3/1973  Fed. Rep. of Germany .
1091734  11/1967  United Kingdom .
1338545  11/1973  United Kingdom .

OTHER PUBLICATIONS

Chimia, vol. 24, (Sep. 1970), pp. 328–342.

Primary Examiner—David B. Springer
Attorney, Agent, or Firm—Oblon, Spivak, McClelland, Maier & Neustadt

[57] ABSTRACT

A process for the preparation of a quinophthalone of the formula

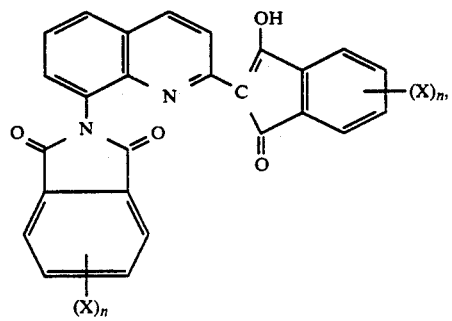

in which X is hydrogen, chlorine or bromine and n is an integer from 1 to 4, by condensing 8-aminoquinaldine with a phthalic anhydride, optionally monosubstituted or polysubstituted by chlorine or bromine, in the presence of molten benzoic acid acting as diluent.

3 Claims, No Drawings

PREPARATION OF QUINOPHTHALONES

The present invention relates to a novel process for the preparation of quinophthalones by condensation of 8-anminoquinaldine with phthalic anhydride optionally monosubstituted or polysubstituted by chlorine or bromine, in the presence of a diluent.

In Chimia 24, 328, 1970 and in GB-A1,091,734, it is proposed to carry out condensation of 2-methylquinoline derivatives (quinaldine derivatives) with aromatic ortho-dicarboxylic acids or their anhydrides in the presence of inert high-boiling diluents such as ortho-dichlorobenzene, trichlorobenzene, nitrobenzene, naphthalene, diphenyl or diphenyl ether.

In addition, DE-A 1,770,960 and DE-A 2,230,601 recommend the co-use of Lewis acids or Broenstedt acids to accelerate condensation.

However, these processes have drawbacks. For example, a reaction temperature of more than 200° C. is usually necessary. As a result, when, in particular, it is desired to produce extremely pure yellow pigments, for example the condensate of 1 mole of 8-aminoquinaldine with 2 moles of tetrachlorophthalic anhydride, partial decomposition of the amino components might cause undesirable dulling necessitating, perhaps, expensive post-purification steps. In order to obtain pigments showing a high degree of brilliance it is necessary to work with an excess of tetrachlorophthalic anhydride (approx. 30 to 50% molar). This excess tetrachlorophthalic anhydride is usually lost when the diluent used is regenerated. Furthermore, some of the diluents proposed, e.g. nitrobenzene or chlorinated benzenes, are not ecologically acceptable.

It is thus an object of the present invention to provide a novel process for the preparation of quinophthalones which no longer suffers from the above drawbacks and is simple to carry into effect industrially. It is a further object to obtain the end products in good yield and to a high degree of purity.

We have now found that the preparation of quinophthalones of formula I

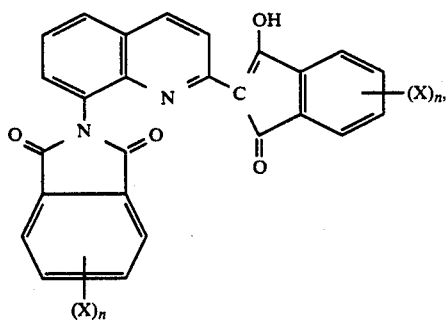

(I)

in which X is hydrogen, chlorine or bromine and n is an integer from 1 to 4, by condensing 8-aminoquinaldine of formula II

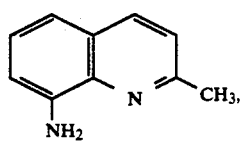

(II)

with a phthalic anhydride of formula III

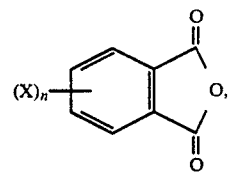

(III)

in which X and n have the meanings stated above, in the presence of a diluent is carried out to advantage when the diluent used is molten benzoic acid.

Suitable phthalic anhydrides of formula III for the process of the invention are, for example, phthalic anhydride, mono-, di-, tri- or tetra-chlorophthalic anhydride and mono-, di-, tri- or tetrabromophthalic anhydride.

the use of tetrachlorophthalic anhydride (X=chlorine, n=4) is preferred.

The process of the invention, which may be carried out batchwise or continuously, is conveniently operated at atmospheric pressure or a slightly elevated pressure (up to about 6 bar). The equipment for carrying out the reaction on an industrial scale may comprise conventional stirred vessels or, if desired, self-cleaning apparatus with positive mixing means. Usually, solid benzoic acid is placed in the reactor and then melted (its melting point is 122.3° C.).

8-Aminoquinaldine and phthalic anhydride III are then added and the mixture is heated to a temperature of from 123° to 200° C. and preferably from 130° to 170° C.

It is particularly advantageous to place benzoic acid and phthalic anhydride III in the reactor and then to meter 8-aminoquinaldine thereto over a period of from 10 to 180 minutes at the temperature proposed by the invention.

Another preferred embodiment of the process of the invention consists in thoroughly mixing benzoic acid, 8-aminoquinaldine and phthalic anhydride III before starting the reaction by heating. In this way, very pure quinophthalones are obtained.

It is also of advantage to carry out heating of the reaction mixture in two stages. For example, the reaction mixture may be initially heated to a temperature of from 130° to 150° C. and then kept at this temperature for about 1 to 3 hours before it is further heated to from 150° to 180° C.

The compounds 8-aminoquinaldine and phthalic anhydride III are generally used in a molar ratio of from 1:2 to 1:3.

For each mole of 8-aminoquinaldine there will usually be used from 0.5 to 20, preferably from 2 to 15, moles of benzoic acid.

Compared with the prior art processes, the process of the invention involves a distinctly lower reaction temperature and a shorter reaction time. This implies that the benzoic acid not only serves as diluent but also accelerates the condensation reaction.

For this reason, the addition of specific catalysts for the purpose of accelerating the reaction does not usually cause any improvement.

On completion of the condensation, which generally takes from 3 to 8 hours, the reaction mixture is cooled to a temperature of from 130° to 150° C., diluted with water, if necessary, and then mixed with a caustic alkali metal solution. e.g. caustic soda solution or caustic potash solution (strength 5 to 20% w/w). The benzoic acid is thus converted to a water-soluble alkali metal benzoate and the quinophthalone of formula I can be isolated by filtration and washed with water.

The benzoic acid can be precipitated from the mother liquor by the addition of acid and then isolated and virtually quantitatively recycled to the condensation. On the other hand, benzoic acid is readily degradable. Together with the benzoic acid, any excess phthalic anhydride III can be virtually quantitatively recovered.

Another working-up procedure is, for example, to place the reaction mixture in an inert organic solvent such as methanol, ethanol, propanol, isopropanol, ethylene glycol momobutyl ether, toluene, xylene or mixtures thereof. The benzoic acid is thus dissolved and the quinophthalones of formula I can be isolated by filtration and washed with the solvent. The benzoic acid can be recovered by evaporating the solvent.

Alternatively, the recovered moist benzoic acid, which may possibly still contain the phthalic acid forming the basis of the phthalic anhydride III, can be directly fed to the process of the invention in the form of an aqueous filter cake, in which case the condensation will be preceded by dehydration to remove water from the reaction mixture and convert the phthalic acid to phthalic anhydride.

Yet another possibility is to omit the phthalic anhydride III and use the corresponding phthalic acid instead, as starting material. Here again, dehydration must precede the reaction in order to form the anhydride.

Our novel process produces good yields of quinophthalones of formula I in a high state of purity.

The quinophthalones obtained by means of the process of the invention are valuable pigments.

The invention is illustrated below by the following Examples.

EXAMPLE 1

270 g of benzoic acid were placed in a stirred reaction vessel and melted. At from 125° to 130° C., there were added to the melt 82 g of tetrachlorophthalic anhydride followed by 19 g of 8-aminoquinaldine. The mixture was heated to 140° C. and stirred at that temperature for 2 hours and then heated to 160° C. and stirred for a further 2 hours. The reaction mixture was then cooled to 130° C. and there was added thereto a mixture of 400 ml of water and 160 g of 50% w/w caustic soda solution. The pigment suspension was filtered in vacuo, washed to neutrality with water and dried. There were obtained 82 g (98%) of quinophthalone of the formula

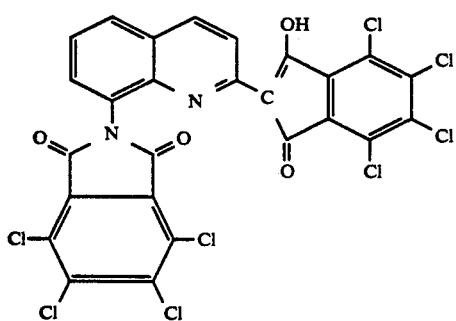

EXAMPLE 2

Example 1 was repeated, except that 122 g of tetrabromophthalic anhydride were used. Yield: 120 g (95%) of quinophthalone of the formula

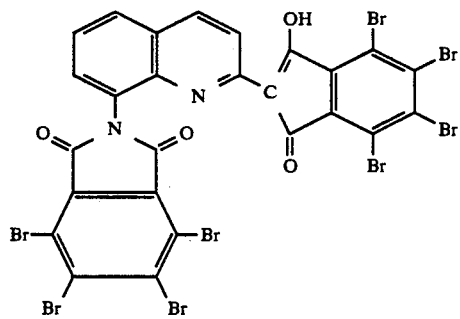

EXAMPLE 3

The moist benzoic acid which was quantitatively recovered from the mother liquor in Example 1 by acidification and precipitation contained 13 g of tetrachlorophthalic acid. This filter cake wa smelted in the reaction vessel, and water was distilled off until the internal temperature reached 115° C. To this melt there were then added 69 g of tetrachlorophthalic anhydride followed by 19 g of 8-aminoquinaldine. The rest of the process was carried out as described in Example 1. Yield 80 g (96%) quinophthalone of the formula

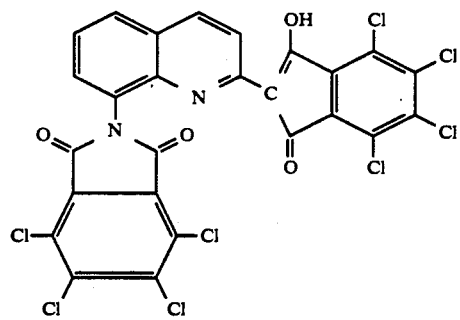

EXAMPLE 4

270 g of benzoic acid and 80 g of tetrachlorophthalic anhydride were placed in a stirred reaction vessel and melted. The mixture was heated to 130° C. with distillation of water and stirring was continued until no more water distilled off (about 2 hours). 19 g of 8-aminoquinaldine were then added and the mixture was heated to 140° C. The rest of the process took place as described in Example 1.

Yield: 82 g (98%) of quinophthalone of the formula

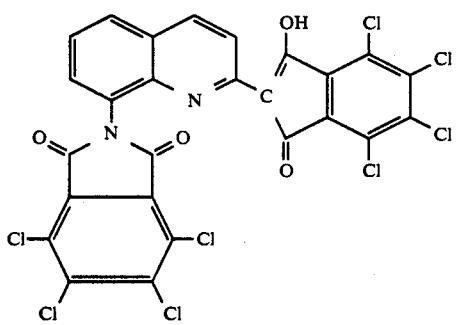

EXAMPLE 5

270 g of benzoic acid, 82 g of tetrachlorophthalic anhydride and 19 g of 8-aminoquinaldine were vigorously mixed, and the mixture was melted in a stirred reaction vessel. The reaction was allowed to proceed for 2 hours at 135° C., after which the mixture was heated to 160° C. and stirring was continued for 2 hours. The reaction mixture was worked up as described in Example 1.

Yield: 82 g (98%) of quinophthalone of the formula

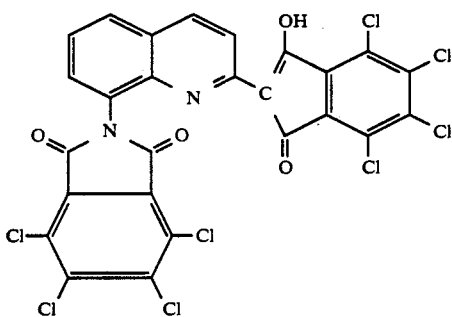

EXAMPLE 6

40 g of benzoic acid, 19 g of 8-aminoquinaldine and 46 g of tetrachlorophthalic anhydride were placed in a paddle dryer, where they were vigorously mixed and heated until molten. The mixture was then slowly heated to 180° C. and then kept at this temperature for 10 hours. The temperature was then reduced to 120° C. and approx. 600 g of 3% w/w caustic soda solution were added. The suspension was discharged and adjusted to a pH of 10.5 with dilute caustic soda solution, after which the pigment was filtered off, washed with water until neutral and dried.

There were obtained 81 g (97%) of quinophthalone of the formula

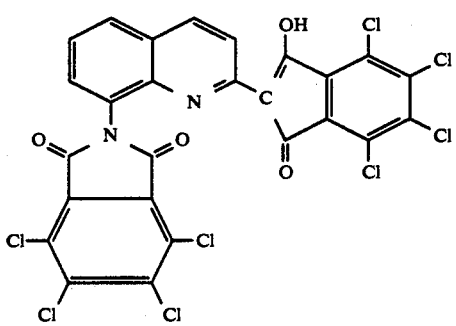

EXAMPLE 7

Example 6 was repeated, except that the reaction mixture was worked up as follows:

It was cooled to 120° C. and 500 g of p-xylene were added. The resulting suspension was discharged and the pigment filtered off and washed with 200 g of p-xylene and dried.

There were obtained 79 g (95%) of quinophthalone of the formula

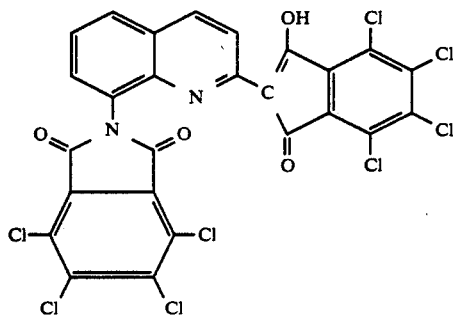

We claim:

1. A process for the preparation of a quinophthalone of formula I

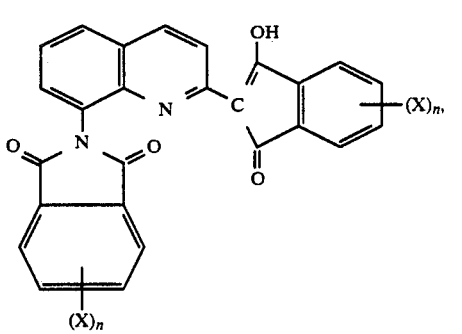

in which X is hydrogen, chlorine or bromine and n is an integer from 1 to 4, by condensing 8-aminoquinaldine of formula II

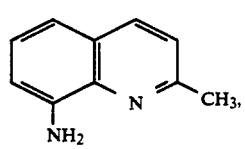

with a phthalic anhydride of formula III

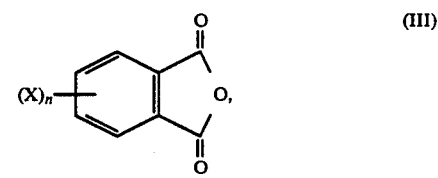

in which X and n have the meanings stated above, in the presence of a diluent, wherein the diluent used is molten benzoic acid.

2. A process as claimed in claim 1, wherein the condensation is carried out at a temperature of from 123° to 200° C.

3. A process as claimed in claim 1, wherein from 0.5 to 20 moles of benzoic acid are used per mole of 8-aminoquinaldine.

* * * * *